(12) United States Patent
Wright

(10) Patent No.: US 7,886,751 B2
(45) Date of Patent: Feb. 15, 2011

(54) CLEANING APPARATUS FOR DENTAL FLOSSING

(76) Inventor: Debbie Wright, P.O. Box 1404, Kalama, WA (US) 98625

( * ) Notice: Subject to any disclaimer, the term of this patent is extended or adjusted under 35 U.S.C. 154(b) by 521 days.

(21) Appl. No.: 11/958,529

(22) Filed: Dec. 18, 2007

(65) Prior Publication Data

US 2009/0151098 A1 Jun. 18, 2009

(51) Int. Cl.
*A61C 15/00* (2006.01)
(52) U.S. Cl. ................................... 132/323
(58) Field of Classification Search ......... 132/321–329, 132/309, 308; 433/141
See application file for complete search history.

(56) References Cited

U.S. PATENT DOCUMENTS 1,820,439 A * 8/1931 Church ................. 132/309
2,754,833 A * 7/1956 Vecchio ................. 132/323
4,397,327 A * 8/1983 Hadary ................. 132/321

* cited by examiner

*Primary Examiner*—Robyn Doan
(74) *Attorney, Agent, or Firm*—Michael Ries

(57) ABSTRACT

A cleaning apparatus capable of being used in dental procedures is disclosed. The cleaning apparatus comprises an elongated handle and a cleaning member. The elongated handle comprises a first end portion and a second end portion. The cleaning member comprises a stretchable member and a brush. The stretchable member has a proximal end portion and a distal end portion. The proximal end of the stretchable member is removably coupled to a connecting point between the first end portion of the elongated handle and the second end portion of the elongated handle. The distal end portion of the stretchable member is slidably engaged to the second end portion of the elongated handle. The brush is attached to the distal end portion of the stretchable member.

2 Claims, 3 Drawing Sheets

CLEANING APPARATUS FOR DENTAL FLOSSING

FIELD OF THE INVENTION

The present invention relates generally to dental appliances, and, more particularly, to a cleaning apparatus used in dental procedures, such as flossing.

BACKGROUND OF THE INVENTION

Cleaning apparatuses such as dental floss are used to remove food and dental plaque from teeth of a person. The dental floss is ordinarily made of soft materials, such as a thin nylon filament or a plastic ribbon. During dental procedures, such as flossing, the dental floss is smoothly inserted between the teeth for scrapping along the teeth sides close to gums. The floss is smoothly wrapped around a tooth and then moved away from the gum line for removing the food and plaque from the teeth. The dental floss can also be used to clean a front or a back side of the tooth.

Presently existing dental flosses used for removing food and the dental plaque from the teeth have numerous limitations. For example, existing dental flosses are difficult to operate when used on persons wearing orthodontic braces over the teeth. Further, these dental flosses are unable to provide and alter a tension in the flosses in order to suit the teeth structure of the different individuals. Further, the existing dental flosses generally require use of fingers to hold the floss in the mouth while flossing.

Therefore, based on the foregoing, there is need for a cleaning apparatus capable of being used in dental procedures, such as flossing, which facilitates a proper removal of food and dental plaque from teeth, generally and also in cases of persons wearing orthodontic braces over teeth. Further, the cleaning apparatus should also be capable of providing and altering proper tension of the floss. Further, the cleaning apparatus should also be capable of avoiding the full insertion of fingers inside the mouth during flossing procedure.

SUMMARY OF THE INVENTION

In view of the foregoing disadvantages inherent in the prior art, the general purpose of the present invention is to provide a cleaning apparatus capable of being used in dental procedures, like flossing, configured to include all the advantages of the prior art, and to overcome the drawbacks inherent therein.

Therefore, an object of the present invention is to provide a cleaning apparatus, which is capable of removing food and dental plaque from teeth of a person, and also from orthodontic braces over the teeth.

Another object of the present invention is to provide a cleaning apparatus which eliminates the full insertion of fingers in a mouth while flossing.

Yet another object of the present invention is to provide a cleaning apparatus, in which tension of a dental floss can be adjusted based on the structure of teeth of different individuals.

Therefore, in one aspect, the present invention provides a cleaning apparatus capable of being used in dental procedures, such as flossing. The cleaning apparatus comprises an elongated handle and a cleaning member. The elongated handle has a first end portion and a second end portion. The cleaning member comprises a stretchable member and a brush. The stretchable member has a proximal end portion and a distal end portion. The proximal end portion of the stretchable member is removably coupled to a connecting point between the first end portion of the elongated handle and the second end portion of the elongated handle. The distal end portion of the stretchable member is slidably engaged to the second end portion of the elongated handle. The brush is attached to the distal end portion of the stretchable member.

These together with other aspects of the present invention, along with the various features of novelty that characterize the present invention, are pointed out with particularity in the claims annexed hereto and form a part of this present invention. For a better understanding of the present invention, its operating advantages, and the specific objects attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE INVENTION

The exemplary embodiments described herein detail for illustrative purposes are subject to many variations in structure and design. It should be emphasized, however, that the present invention is not limited to a particular cleaning apparatus, as shown and described. It is understood that various omissions and substitutions of equivalents are contemplated as circumstances may suggest or render expedient, but these are intended to cover the application or implementation without departing from the spirit or scope of the claims of the present invention.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

Figure 1:
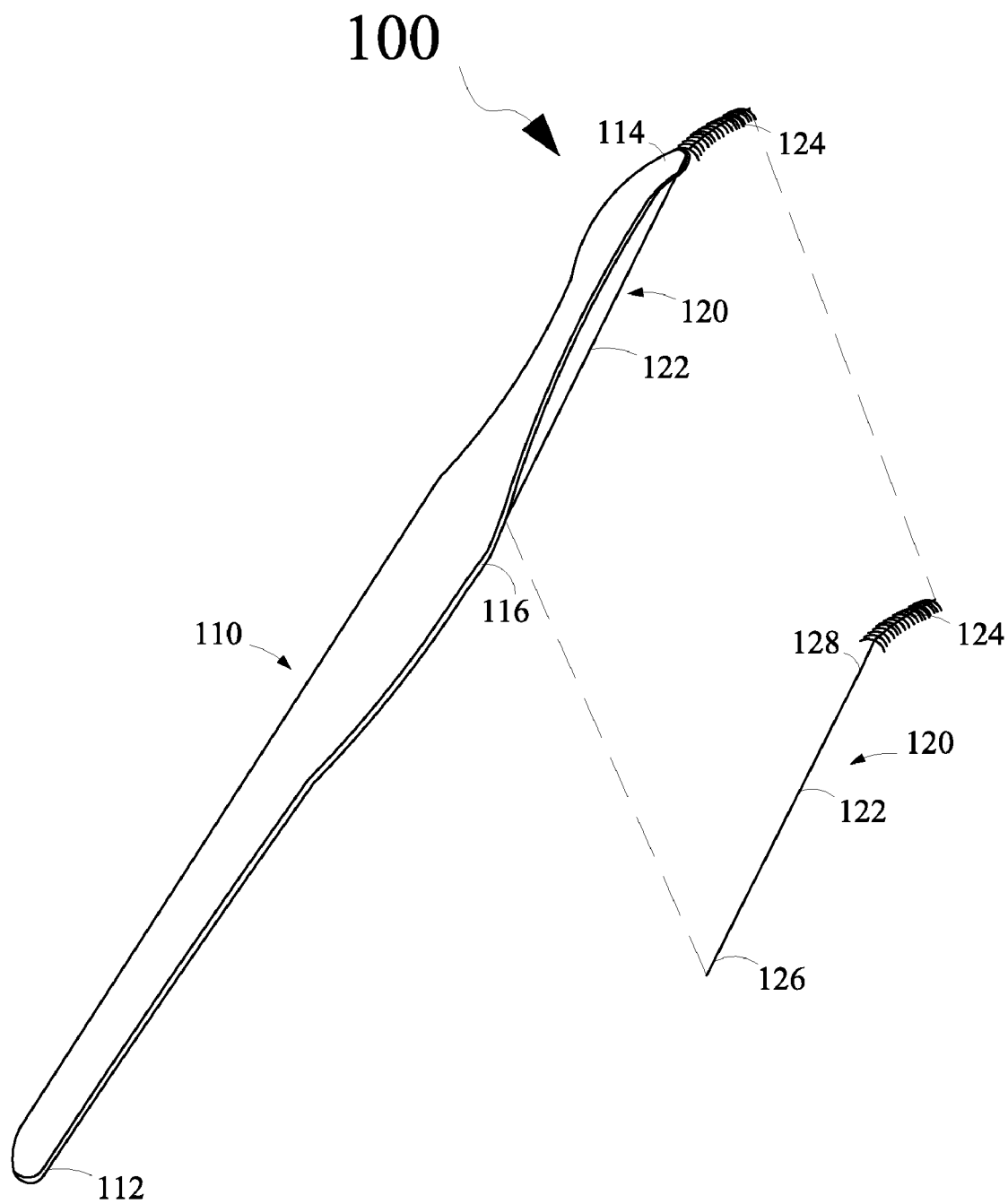
FIG. 1 is a perspective view of a cleaning apparatus, according to an exemplary embodiment of the present invention.

Referring to FIG. 1, a cleaning apparatus 100 capable of being used in dental procedures, such as flossing, is shown. FIG. 1 is a perspective view of the cleaning apparatus 100, according to an exemplary embodiment of the present invention. The cleaning apparatus 100 comprises an elongated handle 110 and a cleaning member 120. The elongated handle 110 may be made of light weight and flexible materials including, but not limited to, rubber, and plastic. Preferably, the elongated handle 110 may be made of non-stick rubber. The elongated handle 110 has a first end portion 112 and a second end portion 114. The elongated handle 110 may have variable width along a length of the elongated handle 110 to provide a firm grip for a user. Additionally, the elongated handle 110 may comprise a gripping element (not shown), which is coupled to the first end portion 112 of the elongated handle 110 and covers a portion of the elongated handle 110 to provide extra grip to the user.

The cleaning member 120 comprises a stretchable member 122 and a brush 124. The stretchable member 122 of the cleaning member 120 is used for cleaning areas between the teeth. As shown in FIG. 1, the stretchable member 122 has a proximal end portion 126 and a distal end portion 128. The proximal end portion 126 of the stretchable member 122 is removably coupled to a connecting point 116 on the elongated handle 110. More specifically, the connecting point 116 lies between the first end portion 112 and the second end portion 114 of the elongated handle 110. The position of the connecting point 116 may be chosen based on a desired length of the stretchable member 122. The distal end portion 128 of the stretchable member 122 is slidably engaged to the second end portion 114 of the elongated handle 110.

In one embodiment of the present invention, the second end portion 114 of the elongated handle 110 may comprise a mechanism, such as an opening (not shown) on the second end portion 114 that facilitates the stretchable member 122 to slide along surface of the elongated handle 110. More specifically, the stretchable member 122 is configured in a manner such that the stretchable member 122 may be pulled outwardly from the second end portion 114 of the elongated handle 110 by applying a force. The stretchable member 122, which is pulled outside of the elongated handle through the through opening, is used for the cleaning purposes during the flossing procedure.

The brush 124 is attached to the distal end portion 128 of the stretchable member 122. The brush 124 is attached with the stretchable member 122 to provide additional cleaning in areas between the teeth. The use of the brush 124 is further described in conjunction with FIG. 3. In one embodiment of the present invention, the stretchable member 122 comprises a floss (not shown) for cleaning between the teeth and an expansion mechanism (not shown) attached with the floss. During the flossing procedure, an overall length of the stretchable member 122 may be adjusted by expanding/compressing the expansion mechanism based on the comfort of the dentist and the person who is undergoing the flossing treatment. An exemplary arrangement of this embodiment is described in detail in conjunction with FIG. 2. However, in another embodiment of the present invention, the stretchable member 122 may be made of a rubber and other elastic materials, which are capable of being stretched by application of a small force by fingers of a hand.

Figure 2:
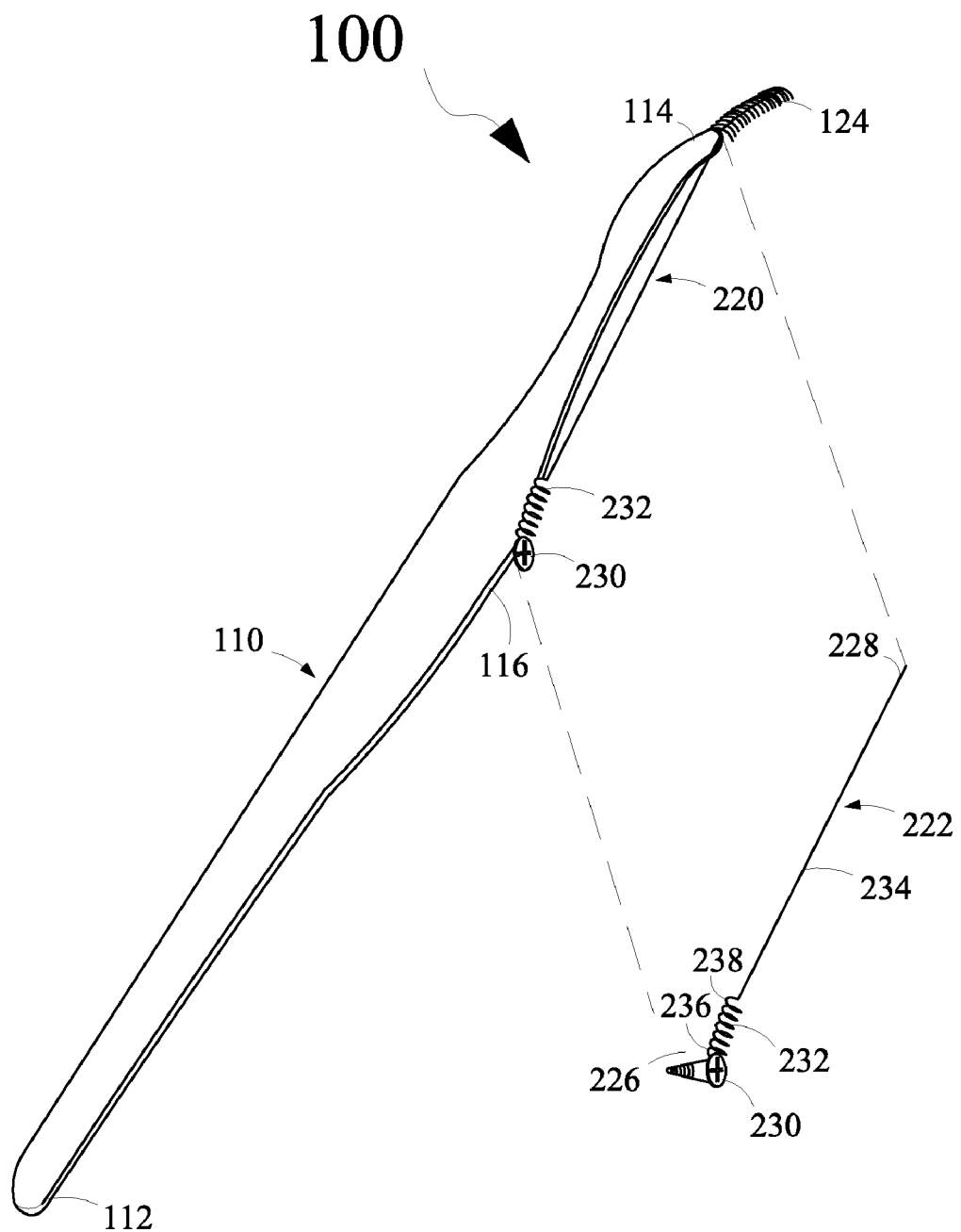
FIG. 2 is a perspective view of a cleaning apparatus, according to another exemplary embodiment of the present invention.

Referring now to FIG. 2, another embodiment of the cleaning apparatus 100 is shown. Herein, an exemplary stretchable member of the cleaning apparatus 100 is represented, which includes a floss for performing the flossing between the teeth and an expansion mechanism, which may be expanded/compressed in order to adjust the length of the floss.

Herein, as represented in FIG. 2, the cleaning apparatus 100 comprises the elongated handle 110 and a cleaning member 220. The cleaning member 220 comprises a stretchable member 222 and the brush 124. The stretchable member 222 has a proximal end portion 226 and a distal end portion 228. The proximal end portion 226 of the stretchable member 222 is removably coupled to the connecting point 116 between the first end portion 112 and the second end portion 114 of the elongated handle 110. The distal end portion 228 of the stretchable member 222 is slidably engaged to the second end portion 114 of the elongated handle 110. As discussed in conjunction with FIG. 1, the second end portion 114 of the elongated handle 110 comprises a mechanism, such as a through opening for providing a sliding movement to the stretchable member 222. The brush 124 is attached to the distal end portion 228 of the stretchable member 222.

The stretchable member 222 comprises a screw 230, a spring mechanism 232 and a floss 234. The screw 230 is disposed at the proximal end portion 226 of the stretchable member 222. The screw 230 is detachably coupled at the connecting point 116 of the elongated handle 110. In an embodiment of the present invention, the screw 230 may be detachably coupled to the elongated handle 110 by means of a threaded hole (not shown) configured in the elongated handle 110. The threaded hole is configured in a manner such that the screw 230 may fit therein and couples to the elongated handle 110. The screw 230 may be coupled to the elongated handle 110 in a variety of ways known in the art. For example, a longitudinal axis of the screw 230 may be perpendicular, parallel or inclined to the elongated handle 110.

The spring mechanism 232 is a stretchable spring structure, such as a coil spring. The spring mechanism 232 has a first end portion 236 and a second end portion 238. The first end portion 236 of the spring mechanism 232 is detachably coupled to the screw 230. The screw 230 facilitates to maintain tension in the spring mechanism 232 by twisting the screw 230 relative to the threaded hole inside the elongated handle 110.

The floss 234 is coupled between the second end portion 238 of the spring mechanism 232 and the brush 124. The floss 234 and the brush 124 are coupled at the distal end portion 228 of the stretchable member 222. Tension of the floss 234 may be adjusted by the tension in the spring mechanism 232. During the flossing procedure in the mouth of a person, the stretchable member 222 may be stretched by pulling the stretchable member 222 outwardly of the elongated handle 110, from the distal end portion 228. More specifically, the length of the stretchable member 222 may be varied due to the expansion or compression in the spring mechanism 232. It will be apparent to a person skilled in the art that the length of the stretchable member 222 may be adjusted to a particular length to assist in the flossing procedure for different individuals.

Figure 3:
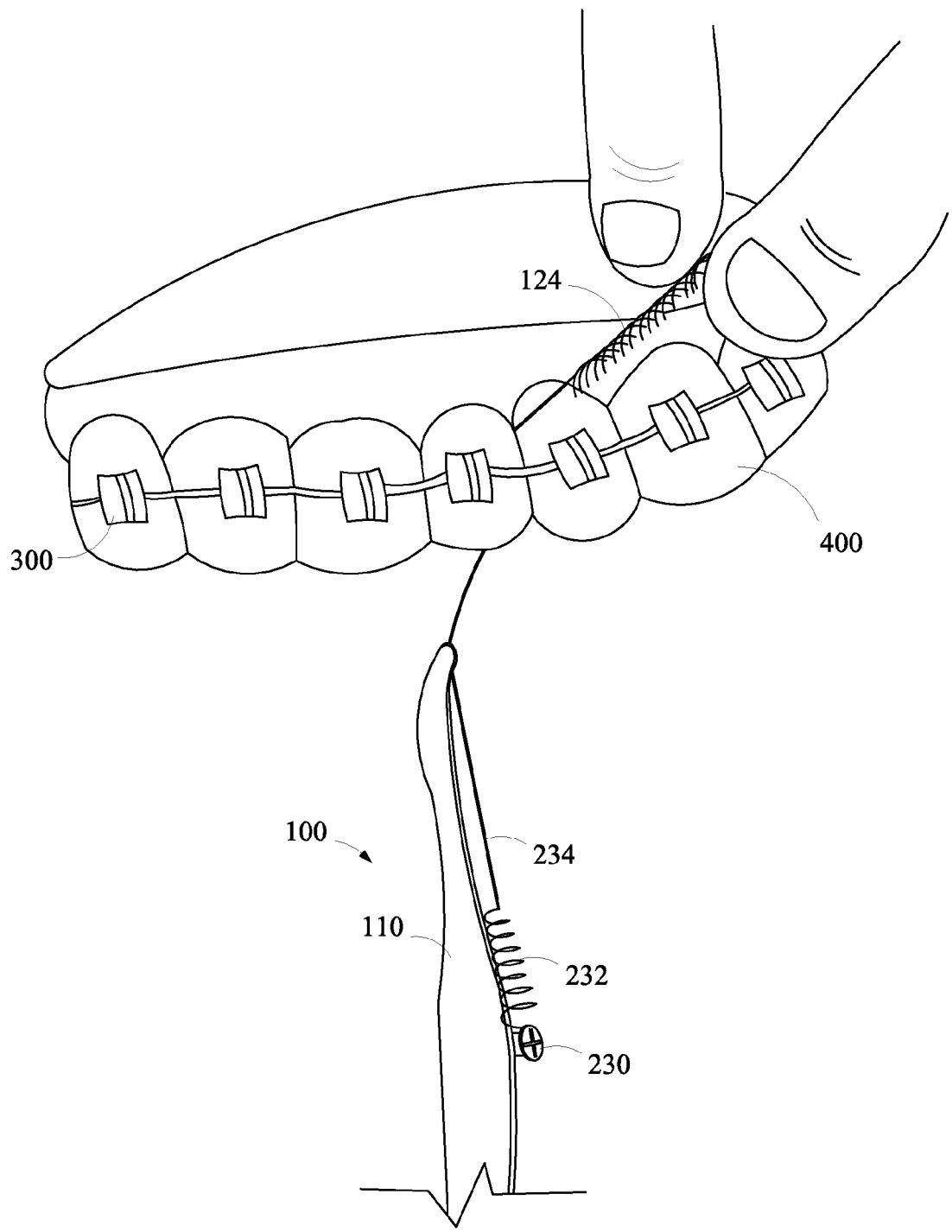
FIG. 3 is a schematic perspective view depicting an application of a cleaning apparatus in removing food and dental plaque from teeth of a person wearing orthodontic braces, according to an exemplary embodiment of the present invention.

The application of the cleaning apparatus 100 in the flossing procedure of teeth of a person is shown in FIG. 3. In FIG. 3, teeth 400 of the person, orthodontic braces 300 over the teeth 400 and the cleaning apparatus 100 is shown. The cleaning apparatus 100 is used for the flossing the teeth 400 and the orthodontic braces 300. The cleaning apparatus 100 is capable of removing food particles and dental plaque from the teeth 400 and the orthodontic braces 300 of the person.

The brush 124 of the cleaning apparatus 100 may be inserted between wires of the orthodontic braces 300 and the teeth 400 of the person. Further, the brush 124 of the cleaning apparatus 100 is clutched with fingers for pulling the stretchable member 122 outwardly from the elongated handle 110 of the cleaning apparatus 100. By keeping proper tension on the stretchable member 122, the stretchable member 122 may be gently inserted between the teeth 400 of the person for flossing. After the completion of the flossing procedure, the stretchable member 122, which is between the teeth 400, is removed. During the flossing procedure, the brush 124 may assist the stretchable member 122 to reach in different areas between the teeth 400. Further, the brush 124 may also act as an additional cleaning element.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the claims of the present invention.

What is claimed is:

1. A cleaning apparatus capable of being used in dental procedures, comprising:
    an elongated handle having a first end portion and a second end portion; and
    a cleaning member comprising,
        a stretchable member having a proximal end portion and a distal end portion, wherein the proximal end portion of the stretchable member is removably coupled to a connecting point between the first end portion of the elongated handle and the second end portion of the elongated handle, and wherein the distal end portion of the stretchable member is slidably engaged to the second end portion of the elongated handle, and
        a brush attached to the distal end portion of the stretchable member
    wherein the stretchable member comprises:
        a screw disposed at the proximal end portion of the stretchable member, the screw capable of being detachably coupled to the elongated handle at the connecting point;
        a spring mechanism detachably coupled to the screw at a first end portion of the spring mechanism, and
        a floss coupled between a second end portion of the spring mechanism and the brush, wherein the floss and the brush are coupled at the distal end portion of the stretchable member.

2. The cleaning apparatus of claim 1, wherein the elongated handle comprises a gripping element coupled to the first end portion of the elongated handle.

* * * * *